United States Patent [19]

Tiholiz

[11] 4,196,196

[45] Apr. 1, 1980

[54] DIVALEN/MONOVALENT BIPOLAR CATION THERAPY FOR ENHANCEMENT OF TISSUE PERFUSION AND REPERFUSION IN DISEASE STATES

[76] Inventor: Ivan C. Tiholiz, 18250 Roscoe Blvd., Northridge, Calif. 91324

[21] Appl. No.: 917,075

[22] Filed: Jun. 19, 1978

[51] Int. Cl.$^2$ .............................................. A61K 37/26
[52] U.S. Cl. .................................................... 424/178
[58] Field of Search ................................. 424/178, 319

[56] References Cited

U.S. PATENT DOCUMENTS

| | | | |
|---|---|---|---|
| 2,781,291 | 2/1957 | Rubin et al. | 424/319 |
| 3,856,771 | 12/1974 | Jackson | 424/178 |
| 4,041,154 | 8/1977 | Helbig et al. | 424/319 |

FOREIGN PATENT DOCUMENTS

| | | | |
|---|---|---|---|
| 4396M | 10/1966 | France | 424/178 |
| 7125666 | 2/1973 | France | 424/319 |
| 786635 | 11/1957 | United Kingdom | 424/178 |

*Primary Examiner*—Frederick E. Waddell
*Attorney, Agent, or Firm*—Martin A. Voet

[57] ABSTRACT

A composition for enhancing vascular perfusion and reperfusion in disease states, both in man and animals comprising an aqueous solution having a slightly acidic pH, and suitable for intravenous use and containing glucose, insulin and Magnesium dipotassium ethylene diamine tetraacetic acid (MgK$_2$ EDTA).

1 Claim, No Drawings

DIVALEN/MONOVALENT BIPOLAR CATION THERAPY FOR ENHANCEMENT OF TISSUE PERFUSION AND REPERFUSION IN DISEASE STATES

BACKGROUND OF THE INVENTION

The invention relates generally to a medical preparation and its use in enhancing tissue perfusion and reperfusion. More specifically, the invention relates to a composition for treating disease processes that involve reduced vascular and tissue perfusion or reperfusion associated with derangement with homeostasis.

BACKGROUND OF THE PRIOR ART

In the past, compositions containing chelating agents such as ethylene diamine tetraacetic acid (EDTA) and its salts has been used or attempted to be used for a wide variety of medical conditions. For example, EDTA has been used in treating urinary calculi (U.S. Pat. No. 3,184,381) and hypertension (U.S. Pat. No. 2,781,291). U.S. Pat. No. 3,838,196 states that EDTA heretofore has been used as a therapeutic decontaminant, as an anticoagulant, to combat digitalis toxicity, to lower serum calcium level in hypercalcemia, to treat scleroderma and for the treatment of arteriosclerosis.

In the past, intravenous solutions have been used to balance or replace specific cations or anions in the body. Typical solutions of this kind are well known in the art.

However, in the field of diseases which have deranged tissue perfusion there has not heretofore been known an intravenous solution which would enhance tissue perfusion and concurrently facilitate the specific divalent/monovalent cation gradients that would enhance homeostasis.

SUMMARY OF THE INVENTION

There has now been discovered a novel, intravenous composition, useful in enhancing tissue perfusion or reperfusion, and also facilitating accumulation and depletion of specific divalent and monovalent cations so as to effect homeostasis in diseased tissue.

The present invention relates to an aqueous solution having a slightly acidic pH, and suitable for intravenous use and containing glucose, preferably in an amount ranging between about 3 to about 25% by weight, insulin, preferably in the approximate ratio of 1 unit of insulin for each 2 grams of glucose in the solution and $MgK_2EDTA$, preferably in an amount to supply from about 0.02 to about 0.04 mEq per Ml of ionic potassium and magnesium.

The present invention also relates to enhancing tissue perfusion in animals and humans by administering intravenously the above solution which contains, per liter, about 10% by weight glucose, about 20 units of insulin and about 6 grams of $MgK_2EDTA$.

The present invention further relates to a method of effecting a change of ionic gradients of calcium, sodium, magnesium and potassium in the serum, interstitial fluid, and tissue cell fluid during the course of the intravenous infusion.

The present invention also relates to a method of temporarily alleviating the symptoms of a disease process involving reduced vascular perfusion by intravenous administration of the above described aqueous solution so as to promote return of the diseased part to homeostasis.

The present invention further relates to a method of effecting rapid renal elimination of calcium and sodium and water while facilitating accumulation of magnesium and potassium in the vascular compartment by intravenous infusion of this aqueous composition.

DETAILED DESCRIPTION OF THE INVENTION

The aqueous composition described herein contains three essential elements: namely, glucose, insulin and Magnesium dipotassium ethylene diamine tetraacetic acid ($MgK_2EDTA$).

Glucose is present in the solution in an amount ranging in concentration from about 3% to about 25% by weight and preferably from about 5 to about 15% by weight and advantageously about 10% by weight.

Insulin is present in the composition in an amount calculated to supply approximately 1 international unit of regular insulin for every 2 grams of glucose in the composition.

$MgK_2EDTA$ is present in the composition so as to yield magnesium and potassium in the solution ranging from about 0.1 mEq per ml to about 0.04 mEq per ml and preferably about 0.02 mEq per ml. The $MgK_2EDTA$ may be made by methods known in the art, such as, for example, as disclosed in U.S. Pat. No. 2,781,291, by dissolving EDTA in potassium hydroxide and combining the resulting potassium EDTA salt in solution with a suitable water soluble magnesium salt such as magnesium chloride. While other salts of EDTA are known, eg., sodium, calcium, etc., the magnesium dipotassium salt described herein is critical to this invention and may not be replaced by any other EDTA salt.

The preferred method of administration is intravenous. For this purpose, the pH of this solution is maintained at a slightly acidic pH, e.g., 6.9 by any suitable means. A typical solution is prepared by adding a suitable amount of 0.1 normal acetic acid to small amounts of a pre-prepared $MgK_2EDTA$ aqueous solution. The resulting solution is added to 1,000 cc of 10% glucose solution (commercially available) at a neutral pH. The required amount of regular insulin is added to the resulting mixture without appreciable change in pH.

Disease processes that are amenable to treatment with the above composition consist of the following:
1. Diseases of diminished vascular capacity.
    a. Arterial
        (1) atherosclerotic cardiovascular disease
        (2) atherosclerotic cerebrovascular disease
        (3) atherosclerotic peripheral vascular disease
    b. Venous
        (1) thrombophlebitis
2. Diseases of diminished tissue perfusion
    a. frostbite
    b. trench foot
    c. myocardial infarction
    d. cerebral infarction
    e. chronic lynphedema
    f. coronary, cerebral, or mesentary thromboses
    g. pulmonary and cerebral embolism
3. Diseases of deranged cation and anion concentration in the various compartments such as:
    a. cardiac arrythmias
    b. hypomagnesemia
    c. hypokalemia
    d. hypernatremia
    e. hypercalcemia f. toxemia of pregnancy
g. delirium tremens
4. Veterinary diseases
 a. red earth disease
 b. Manchester wasting disease
 c. Naalihu disease
 d. La Mancha disease
 e. stiff leg lamb disease The composition herein described is designed to be administered intravenously by conventional means. The amount of solution to be introduced in a particular patient will vary with the patient's age, condition and weight. Preferably the amount of solution to be administered intravenously is approximately 60 drops per minute which would yield approximately 0.24 mEq per minute of potassium and magnesium, 1.2 grams per minute of glucose and 0.6 units per minute of regular insulin for the preferred composition containing about 10% glucose, about 20 units of insulin and about 6 grams of $MgK_2EDTA$.

The rationale for the use of the present composition as hereinbefore described relates to the finding that when $MgK_2EDTA$ is introduced into the slightly alkaline environment of the serum, with the slightly acidic pH of 6.9, a cation shift occurs between the divalent and monovalent cations associated with the EDTA (magnesium and potassium) and the divalent and monovalent cations predominant in the serum (calcium and sodium). The net result is the accumulation of magnesium and potassium in the serum with the calcium and sodium being affixed to the EDTA molecule in a chelation/complexion mode. The EDTA complex thus formed is ultimately excreted into the urine.

The foregoing shift in the serum results in a gradient shift between the serum/interstitial fluid/tissue cell fluid of the calcium and sodium as well as the magnesium and potassium. The movement of the calcium and sodium is into the serum while the gradient effects a movement of magnesium and potassium into the interstitial fluid and further the tissue cell fluid compartments. The concurrent use of glucose and insulin in the solution further assists in the foregoing process by supplying the necessary energy for maintenance of the proper ionic equilibrium across the cell membrane and also accelerates the intracellular movement of carbohydrate and assists in the reestablishment of the Krebs-citric acid cycle.

The following example is for purposes of illustration only and illustration is not to be considered as limiting the invention set forth in the claims appended hereto.

EXAMPLE

The following Example utilizes a left posterior circumflex coronary occlusion to the posterior papillary muscle after the model of Jennings. This model is used to demonstrate the effects of reduced blood flow to the heart. If the occlusion is terminated within 18 minutes of occlusion, no damage is sustained. If the occlusion is not terminated for 40 minutes, approximately 50% damage is sustained. If the occlusion is 60 minutes or longer, 95% of the heart muscle will be damaged.

A 35 kg dog was subjected to a left posterior circumflex coronary occlusion after the model of Jennings. Ten minutes prior to occlusion, during occlusion and 10 minutes following occlusion, an intravenous solution was administered to the dog at the rate of 60 drops per minute. The solution was an aqueous solution containing, for each liter of solution, 10% glucose, 20 units of insulin and 5.87 grams $MgK_2EDTA$. The animal was subjected to an occlusion of 60 minutes. The animal was sacrificed and tissue sections of posterior and anterior papillary muscle of the left ventricle were taken. The findings were that no distinction could be made in the separate heart muscle specimens and there was no evidence of any derangement in the cell structure of either anterior or posterior papillary muscle specimens.

I claim:
1. An aqueous solution for enhancing tissue perfusion or reperfusion in animals and humans comprising about 3 to about 25% glucose, insulin approximately in the ratio of 1 unit of insulin for each 2 grams of glucose and $MgK_2EDTA$ in an amount to supply from about 0.02 to about 0.04 mEq/ml of ionic potassium and magnesium.

* * * * *